US007985830B2

(12) United States Patent
Mance et al.

(10) Patent No.: US 7,985,830 B2
(45) Date of Patent: *Jul. 26, 2011

(54) METHOD FOR MAKING NITROGEN AROMATIC OLIGOMERS AND POLYMERS

(75) Inventors: Andrew M. Mance, Royal Oak, MI (US); Tao Xie, Troy, MI (US); Belabbes Merzougui, Warren, MI (US); Charlene A. Hayden, Bloomfield Hills, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 6 days.
This patent is subject to a terminal disclaimer.

(21) Appl. No.: 12/649,517

(22) Filed: Dec. 30, 2009

(65) Prior Publication Data
US 2010/0105850 A1 Apr. 29, 2010

Related U.S. Application Data

(63) Continuation of application No. 11/230,046, filed on Sep. 19, 2005, now Pat. No. 7,655,749.

(51) Int. Cl.
B01J 23/00 (2006.01)
B01J 23/58 (2006.01)
B01J 23/60 (2006.01)
B01J 23/56 (2006.01)
B01J 23/44 (2006.01)
B01J 23/42 (2006.01)
B01J 23/02 (2006.01)
B01J 23/06 (2006.01)
B01J 23/04 (2006.01)
B01J 23/70 (2006.01)
B01J 23/72 (2006.01)
B01J 23/48 (2006.01)
B01J 23/50 (2006.01)
B01J 23/20 (2006.01)
B01J 23/08 (2006.01)
C07D 213/22 (2006.01)
C07D 213/26 (2006.01)
C07D 237/00 (2006.01)

(52) U.S. Cl. ........ 528/423; 502/308; 502/309; 502/311; 502/312; 502/313; 502/315; 502/317; 502/318; 502/319; 502/320; 502/323; 502/328; 502/329; 502/330; 502/332; 502/333; 502/334; 502/335; 502/337; 502/339; 502/340; 502/343; 502/344; 502/345; 502/346; 502/347; 502/348; 502/349; 502/350; 502/351; 546/259; 546/260; 544/224

(58) Field of Classification Search .................. 502/300; 528/423
See application file for complete search history.

(56) References Cited

U.S. PATENT DOCUMENTS 3,159,641 A 12/1964 Fanshawe et al.
3,421,947 A 1/1969 Wisdom, Jr. et al.
5,922,898 A 7/1999 Miller et al.

FOREIGN PATENT DOCUMENTS

GB 996569 2/1962

OTHER PUBLICATIONS

Yamamoto et al, A Novel Type of Polycondensation Utilizing Transition Metal-Catalyzed C-C coupling. I. Preparation of Thermostable Polyphenylene Type Polymers; Bull Chem Soc Jpn, vol. 51 (7), p. 2091-2097, 1978).*
Usein M. Dzhemilev, et al., Metal Complex Catalysis in a Synthesis of Pyridine Bases, Arkat USA Journal, 2001.
Dr. Roland Winde, The Importance of Homogeneous Catalysis with Precious Metals in Everyday Life, Precious Metals Market Report 3rd Quarter 2002.
Jong-Chan Lee, et al., Rearrangement of the Main Chain of the Organocobalt Polymers, Polymer Bulletin 1997, n.39 pp. 415-422.
Takakazu Yamamoto, et al., A Soluble poly(arylene) with Large Degree of Depolarization, Chemistry Letters, 1998, pp. 153-154.
M. Halim, et al., Measurement of Time Dependent Quantum Yield of poly(p-pyridine) and poly(p-phenylenevinylene), Synethetic Metals 1997, n.84, pp. 951-952.
Meike Reinhold, et al., A Comparison of C-F and C-H Bond Activation by Zerovalent Ni and Pt: A Density Functional Study, J. Am. Chem. Soc. 2004, n.126, pp. 5268-5276.
A. J. Epstein, et al. Poly (p-pyridine)- and poly (p-pyridyl vinylene)-based polymers: Their Photophysics and Application to SCALE Devices, Synthetic Metals, 1996, n.78, pp. 253-261.
Hidekasu Arii, et al., Diiron-polypyridine Complex with Reversible Dioxygen Binding Ability, Department of Applied Chemistry, Nagoya Institute of Technology, Japan, Institute for Molecular Science, Japan.
David J. Irvin, et al., Dual p- and n-type Doping in an Acid Sensitive Alternating bi(ethylenedioxythiophene) and Pyridine polymer, Chem. Comm., 1999, pp. 2121-2122.
M. C. Bernard, et al., Sensitization of TiO2 by a New Polypyridine Dye. Characterization by UV-Vis, FTIR, Raman and EI Spectroscopies, J. Electrochem. Soc., 2003, p. 150.
D. P. Halliday, et al., Visible Electroluminescence from a Polymer Semiconductor Junction, University of Durham, United Kimgdom, 1999.
Antony J. Davies, et al., An Efficient One-pot Synthesis of Annulated Pyridines Utilising a Directed ortho-metallation/transmetallation Approach, Tetrahedron Letters, 2004, n.45, pp. 1721-1724.
S. Dailey, et al., An Efficient Electron-transporting Polymer for Light-emitting Diodes, J. Phys.: Condens. Matter, 1998, n.10, pp. 5171-5178.
Kentaro Masui, et al., Palladium-Catalyzed C-H Homocoupling of Thiophenes: Facile Construction of Bithiophene Structure, J. Am. Chem. Soc. 2004, n.126, pp. 5074-5075.
P. N. Adams, et al., Low Temperature Synthesis of High Molecular Weight polyaniline, Polymer, 1996, v.37 n.15, pp. 3411-3417.
N. V. Smirnova, et al., Formation of Conductive Polymer Films in the Course of Kolbe Reaction: Cathodic and Anodic Polymerization, NATO Advanced Research Workshop on Electrochemistry of Electroactive Polymer Films, 2000.
Alan R. Katritzky et al., Efficient Syntheses of 1-Amido-3-aryl- and 1-Amido-3-alkylimidazo[1,5-a]pyridines, J. Org. Chem., 2001, n.66, pp. 2862-2864.

* cited by examiner

Primary Examiner — Randy Gulakowski
Assistant Examiner — Rachel Kahn
(74) Attorney, Agent, or Firm — Harness, Dickey & Pierce, P.L.C.

(57) ABSTRACT

Methods for synthesizing dimeric or polymeric reaction products of nitrogen aromatics comprise contacting a composition comprising the nitrogen aromatic with a catalyst composition. The catalyst comprises a first metal substrate having a second reduced metal coated on the substrate.

20 Claims, No Drawings

METHOD FOR MAKING NITROGEN AROMATIC OLIGOMERS AND POLYMERS

CROSS-REFERENCE TO RELATED APPLICATIONS

This application is a continuation of U.S. patent application Ser. No. 11/230,046 filed on Sep. 19, 2005. The entire disclosure of the above application is incorporated herein by reference.

FIELD

The present teachings relate to methods of making nitrogen aromatic oligomers and polymers.

BACKGROUND

Activation energy is the minimum energy required to convert the reactants of a chemical reaction into products. When the activation energy is small, kinetic energy from collisions between the reactants can provide the energy required to surmount the activation energy barrier. Conversely, when the activation energy is high, the reaction may require an input of energy, such as heat, and/or alternate means to obtain the products.

Catalysts are often used to facilitate completion of the reaction and/or increase the reaction rate. They function by providing an alternative reaction path having a lower energy of activation. The selection of the catalyst may be based on thermal stability of the reactants and products, energy savings, the raw material, labor and plant process costs, relative yields, and environmental factors. Metals and particularly transition metals are employed as catalysts in a variety of reactions such as the formation of ammonia, production of sulfuric acid, hydrogen addition across alkene or alkyne bonds, ring opening, and polymerization reactions.

Despite their broad uses, use of some metal catalysts still requires that a reaction be performed under extreme conditions because the catalyst alone does not provide a sufficiently low activation energy. Addition of extreme heat and/or pressure generates sufficient kinetic energy to increase the fraction of molecules whose kinetic energy exceeds the activation energy and thereby increase the reaction rate. Also, the use of certain metal catalysts can be cost prohibitive. For example, in some polymerization reactions, zerovalent platinum or palladium may be successfully used to alter the activation energy, but the expense and difficulties of acquiring these metals may make performing the reaction impractical for large-scale applications.

It would be desirable to provide a reagent that has enhanced reactivity, is cost effective, and is easy to manufacture and use. It would also be desirable to have a metal reagent that is able to integrate with and enhance current metal catalysis methods.

It would be further desirable to provide methods to oligomerize and polymerize monomers. It would also be desirable that such methods be conducted at lower temperatures and under atmospheric pressure. It would also be desirable if the methods were cost effective, used inexpensive starting materials, and minimized reaction time.

SUMMARY

The present teachings also provide a method for polymerizing pyridine, comprising contacting a composition comprising pyridine with a catalyst composition, wherein the catalyst comprises a first metal selected from the group consisting of Mg, V, Cr, Zn, Al, Li, Na, K, Be, Ca, Sr, Ba, Ti, Si, and alloys thereof, and the second metal is selected from the group consisting of Ni, Co, Cu, Ti, V, Re, Ru, Rh, Ir, Pd, Pt, Ag, Au, and alloys thereof.

The present teachings also provide methods for producing dimeric nitrogen aromatic products comprise contacting the nitrogen aromatic composition and catalyst composition and reacting for a time sufficient to favor formation of an oligomeric or a polymeric product.

Further areas of applicability of the present teachings will become apparent from the detailed description provided hereinafter. It should be understood that the detailed description and specific examples, while indicating the preferred embodiment of the teachings, are intended for purposes of illustration only and are not intended to limit the scope of the teachings.

DETAILED DESCRIPTION

The present teachings provide a reagent comprising a first metal species substrate having a second reduced metal species coated thereon, where the second reduced metal species is a less electropositive metal than the first metal. As used herein, electropositive refers to the relative standard electrode potentials of the elements. The metals and metallic elements have standard electrode potentials ranging from 3.05 (lithium—most electropositive) to −2.65 (fluorine—least electropositive), with reference to $H_2$ ion as the zero potential couple. The more electropositive metal will reduce the less electropositive metal. For example, an electropositive or active metal, such as zinc (0.76), will tend to reduce a less-active or noble metal, such as copper (−0.34) or silver (−0.80). While not intending to be bound by a particular theory, it is believed that the difference in electropositivity provides a surprisingly effective catalysis as compared to the catalysis action of the metal substrate material or the second reduced metal species material alone.

The first metal species forms the core of the reagent and is selected from the group consisting of alkali metals, alkaline earth metals, transition metals, and metalloids. Various alloys of these metals are also highly suitable in various embodiments. The alloys may be any desirable combination of metals, for example, a Mg alloy according to various embodiments refers to Mg combined with any other metal, such as an Mg/La alloy. Preferred transition metals are from the first transition series (Sc through Zn) and the second transition series (Y through Cd). Preferably, the metal substrate is Mg, V, Cr, Zn, Al, Li, Na, K, Be, Ca, Sr, Ba, Ti, Si, and alloys thereof. In various preferred embodiments, the metal substrate is Mg, V, Cr, Al, Zn, or alloys thereof. In a preferred embodiment, the metal substrate comprises Mg or alloys thereof.

The second metal species is preferably selected from the group consisting of transition metals from the first, second, and third transition series and alloys thereof. It is understood that the second metal may also include any alkali or alkaline earth metal, transition metal, or metalloid that is less electropositive than the metal substrate. This includes using a substrate and a second metal from within the same chemical family, such as two transition metals or two alkaline earth metals. The second metal is in reduced form on the substrate. Preferably, the second metal species is Ni, Co, Cu, Ti, V, Re, Ru, Rh, Ir, Pd, Pt, Ag, Au, or alloys thereof. In various preferred embodiments, the second metal species is Ni, Co, Cu, or alloys thereof.

The second metal species is disposed in reduced form on the substrate core. In various embodiments, the second metal species coats the entire metal substrate core or it covers discrete regions of the core including islands or spots. The second metal species may also be disposed as continuous straight or curved lines, dashed lines, or in a weave or pattern. In various embodiments, the reagent comprises from about 95% to about 99.9% of the first metal species by weight and from about 0.1% to about 5% of the second metal reduced species by weight. Preferably, the reagent comprises about 1% of the reduced species by weight.

In various embodiments, the first metal substrate comprises Mg and alloys thereof and the second metal is selected from the group consisting of Ni, Co, Cu, and alloys thereof. In an alternate preferred embodiment, the first metal substrate is V or alloys thereof and the second metal is selected from the group consisting of Ni, Co, Cu, and alloys thereof.

The metal substrate is of a size suitable for use as a catalyst. In various embodiments, the reagent is in the form of a mesh, a powder, a block, beads, spheres, or turnings. These forms of metal maximize surface area that may be exposed to reactants. Surface area of the metal reagent may range from about 5 nm to about 5 mm. An average dimension (length, diameter, etc.) is less than about 1000 µm. In various embodiments, the average dimension is less than about 500 µm or from about 100 µm to about 400 µm. For example, in an embodiment utilizing a mesh substrate, a preferred size is 40 to 80 mesh. The surface area of the reagent may correlate with the reaction rate. A low surface area reagent tends to catalyze the reaction slower than the same reagent having a greater surface area. A mixture of reagents having different surface areas allows the user to tailor the reaction rate. Furthermore, combinations of metal substrate types and surface areas may also be used, which may provide greater control of catalysis, particularly the reaction rate and temperature.

Methods of Making a Reagent

Methods of making a reagent according to various embodiments of the present teachings are also provided. The method comprises providing a metal substrate and applying a second metal onto the substrate using the metals and metal combinations disclosed earlier herein.

Suitable application techniques include immersion plating, chemical conversion, electroless plating, mechanical plating, detonation gun, plasma arc, vacuum plasma, wire arc, chemical vapor deposition, electron beam evaporation, ion beam assisted deposition, ion implantation, ion plating, physical vapor deposition, sputtering, and vacuum metallizing.

In one embodiment, the application is by immersion plating. Immersion plating involves depositing the second (less electropositive) metal onto the metal substrate without aid of an external electric current. A salt of the less electropositive metal is put into a solution and the solution is contacted with the first metal substrate in suitable form. To illustrate for a cobalt/nickel reagent, cobalt chloride salt, or any other suitable cobalt salt, is put into solution. Suitable solvents include tetrahydrofuran, dimethoxyethane, or other compounds which are able to dissolve the metal salt to some extent without being consumed in the reaction. The solution is contacted with the nickel substrate. As the less electropositive cobalt ions are drawn to the more electropositive nickel substrate, the cobalt deposits onto the nickel substrate forming the reagent.

In another embodiment, the reagent is made by refluxing the metal substrate in the presence of the second metal and a solvent, preferably an organic solvent. Non-limiting examples of suitable organic solvents include tetrahydrofuran and dimethoxyethane. In a highly preferred embodiment, a Soxhlet extractor including a flask, a condenser tube, and a thimble is used. In such an embodiment, the metal substrate is placed into the flask with a solvent. A thimble containing the second metal salt is placed between the flask and the condenser tube. Refluxing the solution from the flask up to the condenser and down through the thimble into the flask again washes the salt in the thimble into the flask where the second metal deposits onto the metal substrate. While not intending to be bound by a particular theory, it is believed that the use of the Soxhlet extractor provides optimal coating results and concentrates the reagent in the flask. It is particularly useful when a minimally soluble metal salt is used as the reagent. Optionally, the reagent is washed and prepared to remove any residue from formation.

One method of forming the catalyst particles in situ is illustrated in the following. Particles made of the first metal are added to a composition containing at least one solvent molecule. The solvent composition is then heated and stirred in the presence of the metal substrate. A salt containing the second metal is then added to the solvent molecule composition containing the first metal particles. The action of heat and stirring causes the second metal to be reduced and disposed onto the surface of the first metal particles. The first metal forms a core onto which the second metal is disposed, preferably at least in part as islands.

The metal substrate may optionally be pre-treated before the application of the second metal species islands. For example, in many cases it is desirable to pre-treat the substrate to remove a passivation layer that builds up on the metal substrate upon exposure to oxygen. In various embodiments pre-treatments involves subjecting the surface to reducing conditions, which renders it more electrochemically active. Alternatively or additionally, current cleaning methods are used. These employ cathodic cleaning where electrical current (which is on the order of about 4 A/cm$^2$ in an exemplary embodiment) is applied to the conductive substrate which is in contact with an electrolyte to facilitate the generation of gas bubbles at the surface. Other pre-treating methods include mechanical abrasion of the surface, or cleaning the substrate with commercially available alkaline cleaners, or pickle liquors. The metal substrate may also be treated with an acidic solution designed to convert the metal oxides to soluble constituents that may be readily removed from the surface. Ultrasonic agitation and high shear mixing may also be used to remove the adherent oxide. In preferred embodiments, the oxide layer is removed by heating the metal substrate to a temperature above the boiling point of the solvent. Adding the solvent to the heated metal substrate volatilizes the solvent and explodes the oxide passivation layer off of the substrate.

Additional pre-treatment or preparation steps may be performed such as metal etching before applying the second reduced metal to increase the substrate surface area. Subsequent treatment steps such as forced-air cooling may also be employed. One skilled in the art understands that variations in any particular pretreatment may be made or other various pretreatments of metals may be used.

Dimeric and Polymeric Reaction Products

Methods for synthesizing dimeric or higher polymeric reaction products of nitrogen containing aromatics are also provided. The method comprises contacting a composition containing the nitrogen aromatic with a catalyst composition described above. The nitrogen aromatic composition comprises a compound or a mixture of compounds represented by the structure:

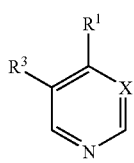

(I)

wherein
X is —N— or —CR²—, and
R¹, R², and R³ are independently selected from the group consisting of hydrogen, alkyl, aryl, heterocyclyl, heteroaryl, and cycloalkyl groups, the groups other than hydrogen having from 1 to 20 carbons. The nitrogen aromatics function as polymerizable monomers. In various embodiments, the compositions further comprise solvent molecules other than the nitrogen aromatic monomer compounds.

The catalyst composition is in particulate form and contains a first metal substrate having a second reduced metal coated on the substrate. In preferred embodiments, the first metal is selected from the group consisting of Mg, V, Cr, Al, Zn, and alloys thereof and the second metal is selected from the group consisting of Ni, Co, Cu, and alloys thereof.

The products of the method are dimeric, oligomeric, or polymeric depending on the reaction conditions. Oligomeric and polymeric products can be homopolymers or copolymers depending on the choice of starting monomers. In a preferred embodiment, polymeric products are homopolymers of pyridine, or copolymers of pyridine and other nitrogen aromatic monomers. Preferably copolymers have greater than 50 mole % pyridine.

In another embodiment, the teachings provide methods for producing dimeric aromatic compounds. The methods involve contacting a composition containing a nitrogen aromatic compound with a catalyst composition as discussed above. The reaction is carried out for a time sufficient to favor formation of a dimeric product over a polymeric product. Preferred aromatic compounds for use in this embodiment of the teachings includes the compounds (I) described above where R¹ is hydrogen. In a preferred embodiment, the nitrogen aromatic compound reaction product is 4,4'-bipyridyl.

In another embodiment, the teachings provide a method for polymerizing pyridine, comprising contacting a composition containing pyridine with a catalyst composition such as those described above. The catalyst preferably contains a first metal and a second metal, with the first metal selected from the group consisting of Mg, V, Al, Cr, Zn, and alloys thereof, and the second metal selected from the group consisting of Ni, Co, Cu, and alloys thereof. In various embodiments, the catalyst is in the form of particles having an average dimension less than 500 μm. As stated above herein, the catalyst is preferably in particulate form having sufficient surface area to catalyze the reaction, particularly polymerization. A preferred first metal is magnesium and a preferred second metal is nickel.

In various embodiments, the method is performed by bringing the catalyst composition into contact with the composition containing the nitrogen aromatic monomers. In other embodiments, the catalyst is formed in the presence of the monomer composition. For example, particles comprising the first metal are added to a pyridine composition, and a salt containing the second metal is added to the pyridine. Heating and stirring of the pyridine composition causes in situ formation of the catalyst and polymerization of the pyridine. In a preferred embodiment, the salt containing the second metal is added to the reaction mixture by way of Soxhlet extraction.

In one aspect, the step of contacting catalyst compositions of the teachings with nitrogen containing aromatic compounds as described affords a general route to dimeric, oligomeric, and polymeric products. The dimeric products are represented by the structure

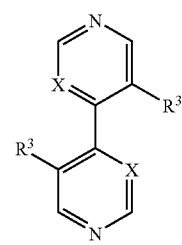

(II)

wherein
X is —N— or —CR²—;
R² and R³ are independently hydrogen or an alkyl, aryl, cycloalkyl, heterocyclyl, or heteroaryl group containing 1 to 20 carbon atoms. Dimeric products arise from the action of the catalyst on nitrogen aromatics wherein R¹ is hydrogen as discussed above. In a preferred embodiment, X is —CR²— and the dimeric products are bipyridyl derivatives.

Oligomeric and polymeric reaction products of the teachings are represented by the structure

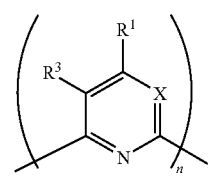

(III)

wherein R¹, R³, and X are as described above and n is 2 or greater. It is to be understood that formulas such as (III) represent the polymeric core or repeating unit of the polymeric or oligomeric reaction product, and is a conventional representation of a polymeric material based on 2,6-polymerization of pyridine or pyrimidine derivatives.

As noted, when R¹ is hydrogen, the nitrogen aromatic starting material can form dimeric products as well as 2,6-oligomeric or polymeric products. In one aspect, the reaction product obtained from the reaction and the relative ratio of dimeric to oligomeric or polymeric products depends on a variety of parameters such as time and temperature of reaction. In one aspect, dimerization to form the dimeric products is reversibly formed in a first fast step. Formation of oligomeric and polymeric 2,6-products on the other hand is slower kinetically, but more thermodynamically favored. In this aspect, longer reactions time tend to favor the formation of oligomeric and polymeric reaction products. Thus, in one aspect of the teachings, dimeric reaction products are prepared by reacting for relatively short times, whereas longer reaction times favor the formation of the polymeric and oligomeric species.

In various embodiments, formation of oligomeric and polymeric products can also be favored by carrying out the reaction in a solvent in which the polymeric products are not soluble. As polymeric compounds are formed they precipitate out of solution and are not further available for kinetically favored dimerization. Thus, the reaction can be carried out in the presence of the monomeric nitrogen aromatics as a sole solvent or in non-reactive solvents such as without limitation acetonitrile, toluene, xylene, 2,6-substituted pyridines and pyrimidines, and the like.

The nature of the polymeric products formed depends on the composition and the relative reaction rates of nitrogen aromatics in the nitrogen aromatic composition that is contacted with catalysts of the teachings. The products can be homopolymers or copolymers. In preferred embodiments, the reaction products are polypyridine or copolymers of pyridine with other pyridine and pyrimidine derivatives such as given above. In preferred embodiments, copolymers contain a major amount of pyridine and a minor amount of other monomers. To illustrate preferred polymers contain 50 mole % or more of pyridine, preferably 75 mole % or more, and more preferably 90 mole % of pyridine or greater. The remainder of the monomeric units is made of nitrogen aromatics other than pyridine. Polypyridine and other nitrogen aromatic polymers are useful for example, as light emitting devices, electroluminescent displays, and in semiconductors.

The n given in the structure of the oligomeric and polymeric materials above ranges from 2 to about 500,000. When n is in the lower part of this range, the compounds an be described as oligomeric. When n is greater than about 5 or 10, the compounds are generally referred to as polymeric. The reaction product mixture resulting from contacting the nitrogen aromatic compounds with the catalyst of the teachings generally contains molecular species characterized by a range of values n, as is familiar to those of skill in the art of polymerization. As is usual in the polymer field, the molecular weight or size distribution of the reaction products can be defined by a molecular weight that depends on n and a molecular weight distribution characterized by a polydispersity.

The catalyst is based on compositions containing at least one less active metal and at least one more active metal. A less active metal is one having a relatively higher reduction potential. In one aspect, the catalyst used for polymerizing the nitrogen aromatics contains a first metal selected from Mg, V, Al, Cr, Zn, and alloys thereof and a second metal selected from Ni, Co, Cu, and alloys thereof. Preferably, the catalyst is in the form of particles having an average dimension of less than 500 µm. In various embodiments, the catalyst is in particulate form that has sufficient surface area to catalyze the polymerization. Also in various embodiments, the first metal forms a core of the catalytic particles and the second metal is disposed in reduced form on the core. In preferred embodiments, the second metal is disposed on the core in such a way as to not cover completely the core. In this embodiment, the second metal is present at least in part as islands of second reduced metal on the first metal core. A preferred material for making the catalyst is magnesium or a magnesium alloy. Magnesium metal is commercially available in particulate form having sufficient surface area to be useful as catalyst of the teachings when coated with a second metal in the way described above. In a preferred embodiment, the second reduced metal disposed on the core is nickel.

In various embodiments, the dimerization, oligomerization, and polymerization reactions are carried out by bringing into contact a composition comprising the catalyst and a composition containing the nitrogen aromatic monomer materials. The catalyst and monomers can be brought into contact in any suitable method. In a non-limiting embodiment, the catalyst particles are prepared in a separate step and added to a composition containing the nitrogen aromatic monomeric materials. In another embodiment, the catalyst particles are formed in situ under the reaction conditions, as discussed earlier herein. In situ formation occurs when a salt of the second metal is added to a composition containing particles of the first metal and a composition containing the nitrogen aromatic compound or compounds. As the nitrogen aromatic composition is heated and stirred as detailed above, the catalyst is formed in situ and the dimerization, oligomerization, and polymerization reactions described above are catalyzed.

The teachings have been described with respect to various preferred embodiments. Further non-limiting description is given in the examples that follow.

EXAMPLES

Example 1

A nickel/magnesium reagent is prepared by the following protocol. The reaction vessel components are first flushed with dry nitrogen gas and the reaction is performed under dry nitrogen gas. 20 grams of 80 mesh Mg metal is placed in a 250 mL 3-neck flask and approximately 140 mL of anhydrous tetrahydrofuran (THF) is added. The flask is connected to a soxhlet extraction apparatus which has an extraction thimble containing 0.5 g of anhydrous nickel bromide. The THF was refluxed for 5 days until the nickel bromide has entirely washed into the flask. Refluxing is halted and the contents of the flask are isolated in a Buchner filter funnel. The solid material is washed several times with THF until the washings are colorless.

The product consists of discontinuous islands of nickel on the surface of magnesium. Chemical analysis shows that the product contains 0.4% by weight of nickel. The rest of the metal content is overwhelmingly magnesium.

Example 2

A reagent is prepared according to Example 1 substituting cobalt chloride for nickel bromide, resulting in magnesium coated with cobalt.

Example 3

All manipulations are performed in a dry inert atmosphere. 20 g of 40-80 mesh magnesium is placed in the thimble of a Soxhlet extractor and washed with anhydrous pyridine for 24 hours. The cleaned metal is then dried by passing dry nitrogen over it.

In a separate step, 0.4 g of anhydrous nickel bromide are weighed out and placed in the thimble of a Soxhlet reactor. 5.0 g of the washed and dried magnesium metal described in the preceding paragraph are placed in a 250 mL round bottom flash. Approximately 140 mL of anhydrous pyridine is added to the flask and the flask is attached to the Soxhlet extractor. The flask is heated to boil (pyridine boils at 114° C.), and nickel bromide is washed into the flask from the Soxhlet extractor for 1 hour. At this point, the contents of the flask are dark blue to black and appear to be increasing in viscosity. The heating is stopped and the flask is allowed to cool. Upon cooling, the contents of the flask solidify. The dark solid is not very soluble in alcohol, acetone, water, tetrahydrofuran, or methylene chloride. The flask is maintained at approximately atmospheric pressure throughout the reaction.

Example 4

The preparation of a nickel magnesium catalyst is carried out as in Example 1. 1.0 g of the catalyst (containing 0.4% by weight nickel) and approximately 140 mL of anhydrous pyridine is added to a 250 mL round bottom flask equipped with a stirring bar and attached to a reflux condenser. The mixture is heated to reflux with stirring. The reflux temperature is approximately 114° C. After an incubation time of 30 minutes the mixture begins to darken. After 60 minutes, the mixture increases substantially in viscosity and is a dark blue.

Example 5

A similar reaction is performed using 5 g of catalysts. The reaction is allowed to run for two hours. At this point the contents of the reaction vessel are completely solidified. A small amount of material identified as 4,4'bipyridyl can be extracted with tetrahydrofuran, pyridine, xylene, or diethyl ether.

Although the teachings have been described above in various exemplary aspects, it is to be understood that the teachings are not limited to the disclosed embodiments. Various modifications that will occur to a person skilled in the art are also within the scope of the teachings.

What is claimed is:

1. A method for polymerizing pyridine, comprising:
   contacting a composition comprising pyridine with a catalyst composition, wherein the catalyst comprises:
     a first metal selected from the group consisting of Mg, V, Cr, Zn, AL, Li, Na, K, Be, Ca, Sr, Ba, Ti, Si, and alloys thereof, and
     a second reduced metal coated over the first metal, wherein the second metal is selected from the group consisting of Ni, Co, Cu, Ti, V, Re, Ru, Rh, Ir, Pd, Pt, Ag, Au, and alloys thereof.

2. The method according to claim 1, wherein the catalyst is in the form of particles having an average diameter of less than about 500 μm.

3. The method according to claim 1, wherein the catalyst is in particulate form and has sufficient surface area to catalyze a polymerization, the first metal forms a core of the catalyst particles, and the second metal is disposed on the core.

4. The method according to claim 3, wherein the first metal comprises Mg or alloys thereof.

5. The method according to claim 3, wherein the first metal comprises Mg or Mg alloy and the second metal comprises Ni, Cu, Co, or alloys thereof.

6. The method according to claim 1 further comprising adding the catalyst composition to the pyridine composition.

7. The method according to claim 1, comprising forming the catalyst in the presence of the pyridine composition.

8. The method according to claim 7, comprising adding particles comprising the first metal to the pyridine composition and adding a salt comprising the second metal to the pyridine composition.

9. The method according to claim 8, comprising Soxhlet extraction of the salt into the pyridine.

10. A method for producing oligomeric nitrogen aromatic products comprising:
   a) contacting a composition comprising a nitrogen aromatic with a catalyst composition; and
   b) reacting for a time sufficient to favor formation of an oligomeric product over a dimeric product,
wherein the nitrogen aromatic comprises a compound or compounds represented by the structure

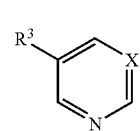

(I)

wherein
X is —N— or —CR$^2$—; and
R$^2$ and R$^3$ are independently selected from the group consisting of hydrogen and alkyl, aryl, heterocyclyl, heteroaryl, or cycloalkyl groups containing 1 to 20 carbons; and the catalyst composition comprises a first metal substrate having a second reduced metal coated on the substrate, wherein the first metal is selected from the group consisting of Mg, V, Cr, Zn, Al, Li, Na, K, Be, Ca, Sr, Ba, Ti, Si, and alloys thereof, and the second metal is selected from the group consisting of Ni, Co, Cu, Ti, V, Re, Ru, Rh, Ir, Pd, Pt, Ag, Au, and alloys thereof.

11. The method according to claim 10, wherein the catalyst is in a form selected from a mesh having a mesh size of from 40 to 80 mesh or particles having an average diameter less than about 500 μm.

12. The method according to claim 10, wherein the catalyst is in particulate form and has sufficient surface area to catalyze a polymerization, the first metal forms a core of the catalyst particles, and the second metal is disposed on the core.

13. The method according to claim 12, wherein the first metal comprises Mg or Mg alloy and the second metal comprises Ni, Cu, Co, or alloys thereof.

14. The method according to claim 10, further comprising adding the catalyst composition to the pyridine composition.

15. The method according to claim 10, further comprising forming the catalyst in the presence of the pyridine composition.

16. A method for synthesizing higher polymeric reaction products of nitrogen aromatics, comprising: contacting a composition comprising the nitrogen aromatic with a catalyst composition, wherein the nitrogen aromatic composition comprises a compound or a mixture of compounds represented by the structure

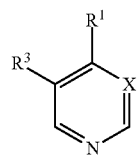

(II)

wherein
X is —N— or —CR$^2$—;
R$^1$, R$^2$, and R$^3$ are independently selected from the group consisting of hydrogen or alkyl, aryl, heterocyclyl, heteroaryl, or cycloalkyl groups containing 1 to 20 carbons; and
wherein the catalyst composition is in particulate form having an average diameter less than about 500 μm and comprises a first metal substrate having a second reduced metal coated on the substrate, wherein the first metal comprises Mg or Mg alloy and the second metal comprises Ni, Cu, Co, or alloys thereof.

17. The method according to claim 16, wherein the contacting is performed in a solvent selected from the group consisting of: acetonitrile, toluene, xylene, pyridine, pyridimine, and combinations thereof.

18. The method according to claim 16, wherein the reaction product comprises a copolymer of pyridine and a different aromatic nitrogen compound.

19. The method according to claim 16, further wherein the reaction product comprises at least 50 mole % pyridine.

20. The method according to claim 16, wherein the catalyst comprises from about 0.1 to about 5% of the second reduced metal by weight.

* * * * *